(12) United States Patent
Ramsauer

(10) Patent No.: US 7,543,988 B2
(45) Date of Patent: Jun. 9, 2009

(54) X-RAY DEVICE FOR IMAGING AT LEAST ONE PART OF AN EXAMINATION OBJECT

(75) Inventor: Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/606,163

(22) Filed: Nov. 29, 2006

(65) Prior Publication Data

US 2007/0139799 A1    Jun. 21, 2007

(30) Foreign Application Priority Data

Dec. 1, 2005    (DE) ........................ 10 2005 057 371

(51) Int. Cl.
    *A61B 6/08*    (2006.01)
(52) U.S. Cl. ......................................... 378/206; 378/37
(58) Field of Classification Search ...................... 378/9, 378/37–38, 206, 166, 205; 362/120
    See application file for complete search history.

(56) References Cited

U.S. PATENT DOCUMENTS

| 4,259,585 | A | * | 3/1981 | Novak et al. .................. 378/37 |
| 5,320,111 | A | * | 6/1994 | Livingston .................... 600/567 |
| 5,661,775 | A | * | 8/1997 | Cramer et al. ................ 378/206 |
| 5,702,175 | A | * | 12/1997 | Chen ........................... 362/191 |
| 6,041,249 | A | * | 3/2000 | Regn ............................ 600/429 |
| 6,305,842 | B1 | | 10/2001 | Kunert |
| 6,505,842 | B2 | | 1/2003 | Butterfield et al. |
| 6,819,738 | B2 | * | 11/2004 | Hoffman ........................ 378/19 |
| 2004/0131157 | A1 | | 7/2004 | Stevanovic et al. |
| 2005/0069092 | A1 | | 3/2005 | Xiaodong et al. |

FOREIGN PATENT DOCUMENTS

| CH | 684737 A5 | 12/1994 |
| DE | 10 2004 001 183 A1 | 7/2004 |
| DE | 10 2004 046 035 A1 | 4/2005 |
| EP | 547377 A2 | 7/1993 |

* cited by examiner

*Primary Examiner*—Hoon Song
(74) *Attorney, Agent, or Firm*—Brinks, Hofer, Gilson & Lione

(57) ABSTRACT

An X-ray device for imaging at least one part of an examination object. The X-ray device includes a support arm that supports an emitter head and an X-ray detector. The emitter head includes an X-ray source. A first light source is operative to illuminate a surface, which is to be irradiated by the X-ray source, of the examination part of the examination object. A second light source is operative to illuminate a work region in which the part of the examination object is positioned during the imaging.

21 Claims, 2 Drawing Sheets

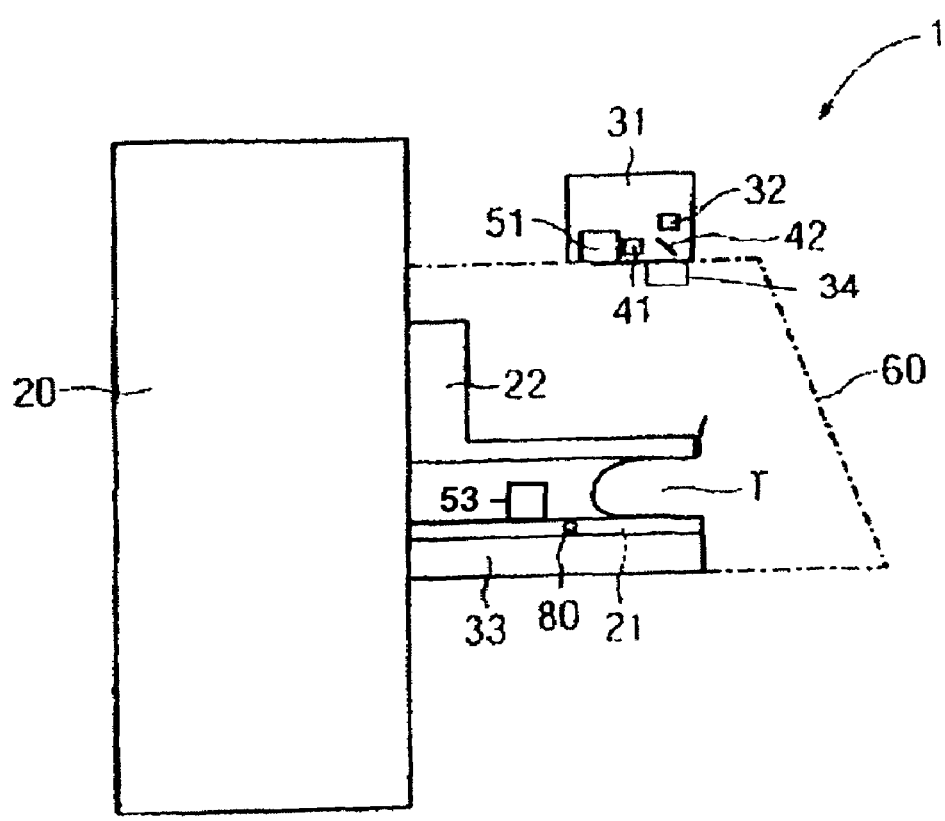
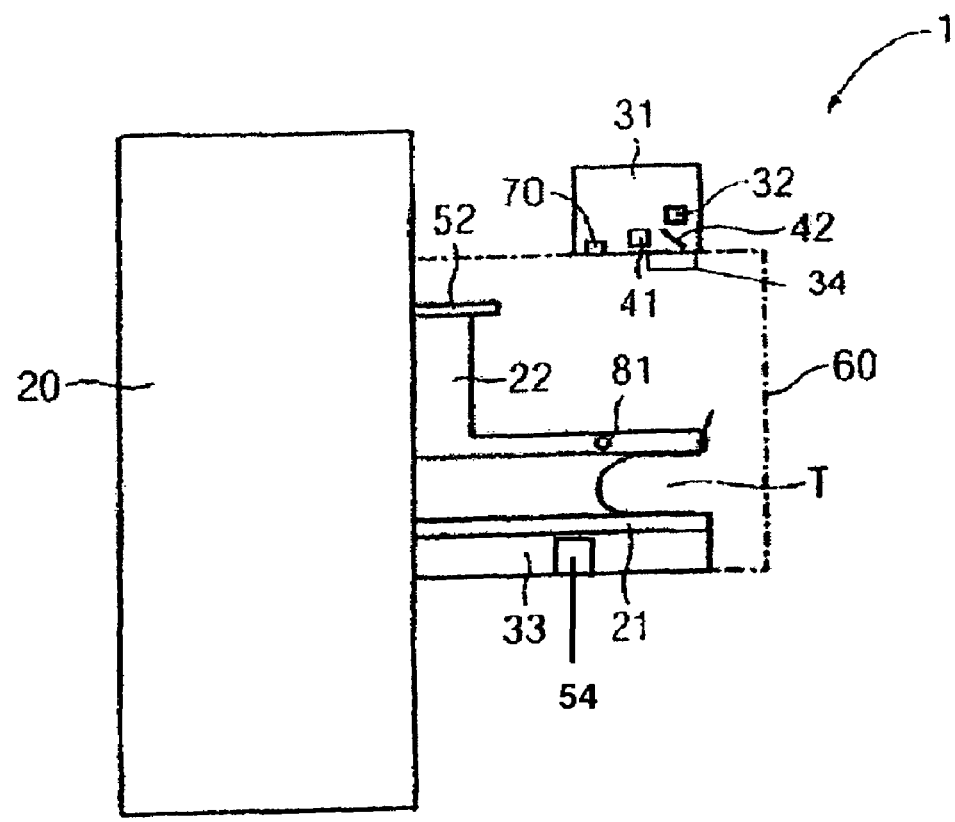

X-RAY DEVICE FOR IMAGING AT LEAST ONE PART OF AN EXAMINATION OBJECT

The present patent document claims the benefit of the filing date of DE 10 2005 057 371.1, filed Dec. 1, 2005, which is hereby incorporated by reference.

BACKGROUND

1. Field

The present embodiments relate to an X-ray device for imaging at least one part of an examination object.

2. Related Art

The present embodiments relate to the field of medical technology. X-ray systems remain a significant instrument for medical diagnosis and patient monitoring regardless of the development in the field of medical technology, and in particular imaging methods, such as computed tomography and magnetic resonance tomography. Mammography systems, for example, provide information about the condition of breast tissue and are used for breast cancer screening.

X-ray examinations are also used in diagnosing, for example, bone fractures, tumors, cysts, calcifications, or air inclusions. Angiographic examinations are used for detecting the vascular system of a patient. Medical instruments that have been introduced into a patient's body can also be located and monitored using X-ray examinations during interventional actions. When the radiation dose used for the X-ray examinations of the patient is reduced, for example, by technological or technical progress, still other fields where X-ray diagnosis can be used are gained (possible).

In radiology equipment for diagnosis, the mobility of the equipment is of increasing significance, so that examinations may be completed independently of a fixed location. The device (equipment) should operate independently of external factors, for example, the power supply that generates X-radiation, the display device, and lighting the object.

U.S. Pat. No. 6,305,842 B1 discloses an X-ray device which has an X-ray source and diaphragms that define an X-ray cone. The X-ray device also has a light source that generates a light cone, which passes through the same diaphragm opening using a mirror. The device is able to trace (mimic) the surface, which is irradiated by the X-radiation, using visible lighting.

According to U.S. Pat. No. 6,305,842 B1, the visible lighting serves only to display the region to be examined. There are structural limitations to the device and/or the light source which adversely affect the lighted surface, the luminous intensity, and possibly the duration of the lighting. The light source is difficult to replace if it should fail. The service life of the light source is reduced when the light source is used in a different field, for example, not in accordance with its original task.

SUMMARY

The present embodiments may obviate one or more of the limitations of the related art. For example, in one embodiment, an X-ray device for imaging a part of an examination object includes a support arm that supports an emitter head and an X-ray detector. The emitter head includes an X-ray source. A first light source is operative to illuminate a surface, which is to be irradiated by the X-ray source, of the part of the examination object.

In one embodiment, a second light source is provided, which is operative to illuminate a work region in which the examination part of the examination object is positioned during the imaging. The intensity of the lighting, for example, the brightness, at the work region, is the physical variable known as luminous intensity. The luminous intensity is the incident luminous flux per unit of surface area.

The luminous intensity is a photometric variable; for example, it takes into account the function of sensitivity to brightness that the human eye has. The luminous intensity is a receiver variable and may be ascertained (acquired) as needed at a definable measurement site by a measuring instrument.

In one embodiment, the work region is the object table and the space located above it. Alternatively, the work region may also include the surroundings of the X-ray device, for example, if that the surrounding area is needed for the work to be done.

In one embodiment, a second light source is operative to illuminate a work region. In this embodiment, the illumination of the medical work site or work region is increased. In one embodiment, the luminous flux of the second light source is controllable. In this embodiment, the brightness or luminous intensity in the work region may be adapted to the type of viewing task or to the jobs that are to be performed. This may be accomplished by a dimmer. For example, one suitable dimmer is a potentiometer. In this embodiment, the service life of the first light source may not be shortened by the use in a different field. For example, the first light source may be used for marking a surface, which is to be irradiated by the X-ray source, of the part to be examined of the examination object and other suitable purposes.

The second light source may be used in any suitable system. For example, one suitable system is the C-arch X-ray device, which is used in monitoring medical interventions, and in which improved work site conditions from the standpoint of light are advantageous. Another suitable system is a computed tomography (CT) system. Light sources are helpful, for example, if the CT system is used to monitor a biopsy. The present embodiments may be used in, for example, mammography equipment and other conventional 2D X-ray devices.

In one embodiment, the second light source has a greater luminous intensity than the first light source. For example, the first light source is embodied and adapted to mark the beam field. The first light source may include, for example, a point source, which has a low radiation intensity. Generally, the radiation intensity required to properly light a work region is greater than the radiation intensity created from the point source. In one embodiment, the second light source, which is embodied to light the work region, has a higher luminous intensity than the first light source. Because of the higher luminous intensity, greater brightness in the work region is obtained, and as a result, improved working conditions.

In one embodiment, the second light source has a light cone (illumination area) with a larger opening angle than the first light source. The opening angle of the first light source is the area irradiated by the first light source in the work region that is equal to the area that is irradiated by the X-ray source. In this embodiment, the first light source is not used variably for lighting the work region because only a portion of the work region is illuminated. The light cone (illumination area) of the second light source has a larger opening angle than the opening angle of the X-radiation beam field and the light cone of the first light source. Using the second light source, the illumination inside the entire work region can be made brighter, even beyond the examination part of the examination object.

In one embodiment, the opening angle of the light cone of the second light source is variable using, for example, a diaphragm. The size of an area to be irradiated in the work region may be selected. For example, not only the examination part of the examination object can be irradiated, but also the surroundings, by widening the opening angle of the second light source beyond the boundaries of the examination part to be lighted of the examination object.

Alternatively, a reduction in the opening angle of the light cone of the second light source may be obtained. For example, in biopsies, only a small area of the examination object is irradiated with a high luminous intensity. Accordingly, the preparation for biopsies that use an X-ray device may benefit from a light that is able to reduce the opening angle. The lighting angle and brightness of light in the work region is not limited to the disclosed embodiments, rather the lighting angle and brightness can take any suitable angle or intensity, respectively. For example, the lighting opening angle and brightness may be adapted to particular job to be done and object to be examined by the medical personnel.

For example, fine work requires a higher luminous intensity than coarse work, and dark objects require a higher luminous intensity than light objects. Older people also require more light than younger ones, for the same visual power. Contrast sensitivity, visual acuity, and the speed of perception of the human eye also depend on the luminous intensity. In one embodiment, both a high luminous intensity and a large illuminated area are used.

In one embodiment, the second light source is secured to the support arm. By mounting the second light source on the support arm, direct lighting of the work region or of the examination object is made possible. In one embodiment, the base of the light source may be both reflective and rotatable. A wider light beam of high intensity may be rotated in any suitable direction.

In one embodiment, the position of at least one second light source is adjustable. In this embodiment, the at least one second light source is coupled to, for example, a movable carriage, which is disposed on the support arm. The position of the second light source may always be adjusted such that there are no visual obstacles in the beam path of the second light source. In this embodiment, the best possible lighting of the work region, for example, a biopsy needle, may be obtained.

In one embodiment, the user operation of the second light source is controlled by the system. For example, the user operation of the second light source, such as turning it on and off, adjusting the position, and adjusting a projection direction of the light, and the like is controlled at a device, for example, a biopsy unit, which is required to perform an examination and/or a treatment. In one embodiment, contact-free or contactless operation of the second light source is possible. For example, during a sterile examination, such as a biopsy, the operation of the second light source is possible without contaminating the working region. In this embodiment, contact with potentially germ-contaminated components of the X-ray device is avoided. In one embodiment, at least one light source may be integrated into, for example, the biopsy unit, to attain further improvement in the working conditions in terms of lighting in a biopsy.

If a plurality of light sources are used for lighting the work region, they can be disposed on the support arm—for instance at different support arm positions or directions—so that the work region is always ideally lighted.

In one embodiment, a defective light source may be quickly and simply replaced. For example, if one second light source is defective and is mounted on the support arm so as to be accessible from outside the system, then the defective light source can be replaced quickly and simply by a functioning light source.

In one embodiment, the second light source is secured to the emitter head. In this embodiment, the second light source shines virtually perpendicularly onto the object table. Because of the substantially vertical incidence of the light with regard to the surface of the object table, unwanted shading can be reduced or even eliminated entirely. The quality of the lighting can thus be enhanced still further.

In another embodiment, if the second light source is mounted on the emitter head so as to be accessible from outside. A defective light source may be replaced quickly and simply by a functioning light source. If the emitter head is displaced or rotated, for example, in examinations using X-ray devices that are capable of tomography, then the light source is also displaced or rotated during the examination.

In one embodiment, the examination part of the object to be examined is visible using the work region lighting. During examinations, which involve displacement of the emitter head of the X-ray device toward the examination object or toward an examination part of the examination object, such as in peripheral digital angiography, the examination part of the examination object can be made visible by the work lighting. In this embodiment, the work region of the region of interest of the examination object is well illuminated.

In one embodiment, the second light source includes a light-emitting diode. Light-emitting diodes have high efficiency and can optionally be varied in terms of the color of their light. Light-emitting diodes have low energy consumption and a long service life. Alternatively, incandescent lamps, for example, low-voltage incandescent halogen lamps, candle lamps, round bulb lamps, and other suitable lighting sources may be employed. In one embodiment, the light source has a transparent covering to protect against soiling.

In one embodiment, a deflection device is operable to guide the beam of light. A deflection device, for example, a waveguide or mirror, is used so that the position and/or location of the second light source may be freely selected. In one embodiment, the beginning and ending of the light, for example, turning the second light source on and off, is controlled by a switch, which is operated manually by hand and/or foot.

In one embodiment, the light source can be switched off without separate manual operation, for example, after a length of time that can be adjusted by the user. A variable definition of the beginning and end of the work region lighting, switching off the light source even though the work in the work region has not yet been concluded is avoided, since the duration of lighting can be adapted to the work to be done. Alternatively, the light source can be switched on whenever motion in the work region is detected by a motion sensor, mounted for instance on the emitter head.

BRIEF DESCRIPTION OF THE DRAWINGS

FIG. 3 is a side view of the embodiment shown in FIG. 1 with a second light source mounted on the examination table.

FIG. 4 is a side view of the embodiment shown in FIG. 2 with a second light source mounted below a transparent surface of the examination table.

DETAILED DESCRIPTION

Figure 1:
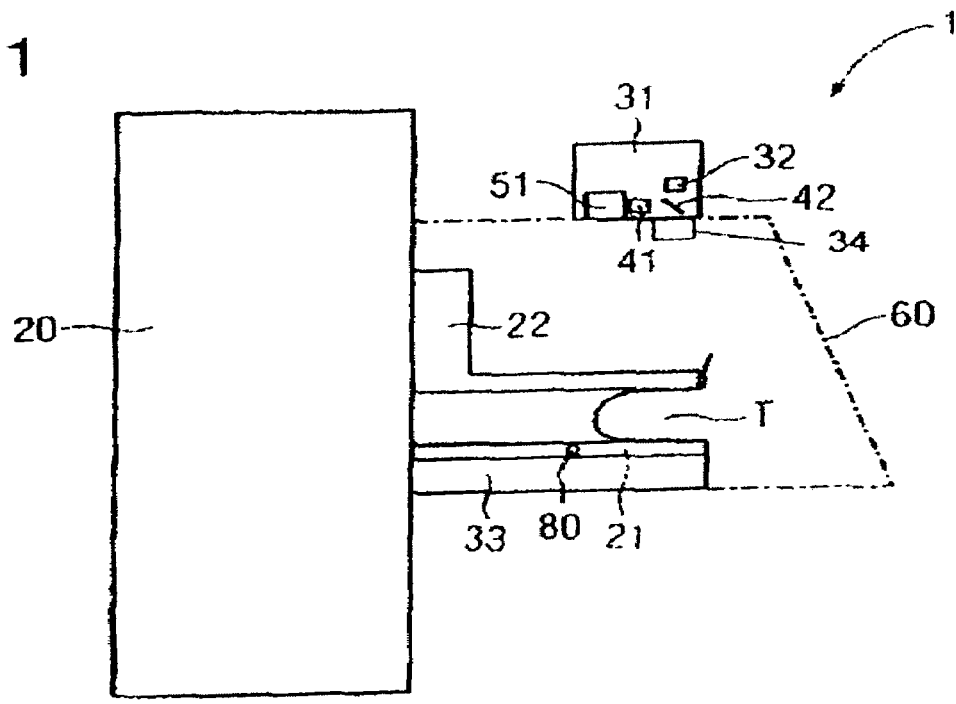
FIG. 1 is a side view of one embodiment of an X-ray device with a second light source mounted on the emitter head.

In one embodiment, as shown in FIG. 1, the X-ray device 1 is a mammography device. The X-ray device 1 includes a support arm 20 on which an object table 21 and a compression unit 22 are mounted. An emitter head 31 is disposed above the object table 21. The emitter head 31 has an X-ray source 32. The X-radiation generated by the X-ray source 32 is emitted in the direction of the object table 21 through the opening in a diaphragm 34 and in the process shines through the part T of the examination object that is positioned on the object table 21.

In one embodiment, the X-radiation is detected by an X-ray detector 33 disposed below the object table 21. A first light source 41 is installed in the emitter head 31. The first light source 41 may include a point source. The first light source 41 displays (illuminates) the surface region through which the X-radiation shines when it is operated. The first light source 41 can be activated by a control key.

In one embodiment, when the first light source 41 is activated, a mirror 42 is pivoted into the beam path of the first light source 41 and deflects the light from the first light source 41 in the direction of the object table 21. The light from the first light source 41 passes through the opening in the emitter head 31 and also passes at least partway through the opening in the diaphragm 34. The beam field of the X-radiation is projected by the light source 41 as a light marking on the object table 21, or the part T of the examination object.

In one embodiment, a second light source 51 is mounted on the emitter head 31. The second light source 51 may be switched on manually. The second light source 51 illuminates the work region 60. For example, if work must be done on the examination object or on the object table 21 before or during the X-ray examination, such as preparation work for a biopsy, then the second light source 51 may be used. The second light source 51 may include a number of light-emitting-(LEDs), which emit light in various directions. The colors of the emitted light can be selected arbitrarily. For example, white light may be used to make an adequate luminous intensity available, or warm colors can be used for creating a pleasanter examination atmosphere. The work region 60 is well-illuminated as a result of using the second light source 51.

In one embodiment, the second light source 51 may be controlled (i.e. switching on and off) using a user-control device 80. As shown in FIG. 1, the user-control device 80 is located near the examination part T of the examination object on the object table 21. The user-control device 80 is embodied as a control button that can be recessed into the object table 21. In one exemplary embodiment, the control button 80 may be operated during the compression of the breast, without requiring that the medical worker change his position to operate the control button 80. In one embodiment, inadvertent actuation of the control button 80 is reduced because the control button 80 is embodied in a sunken fashion in the object table 21.

In one embodiment, the illuminated work region 60 may be expanded to illuminate a larger area. In this embodiment, the illuminated work region 60 may be adapted to the individual project to be completed and the X-ray device 1 used. In this embodiment, the medical worker is able to perform jobs, for example, biopsies, with an adequate luminous intensity.

In one embodiment, various LEDs 51 may shine on essential points in the work region 60. The essential points in the work region 60 may be, for example, the examination part T of the examination object, the device for furnishing medical instruments, or a display of examination parameters on the X-ray device 1.

Figure 2:
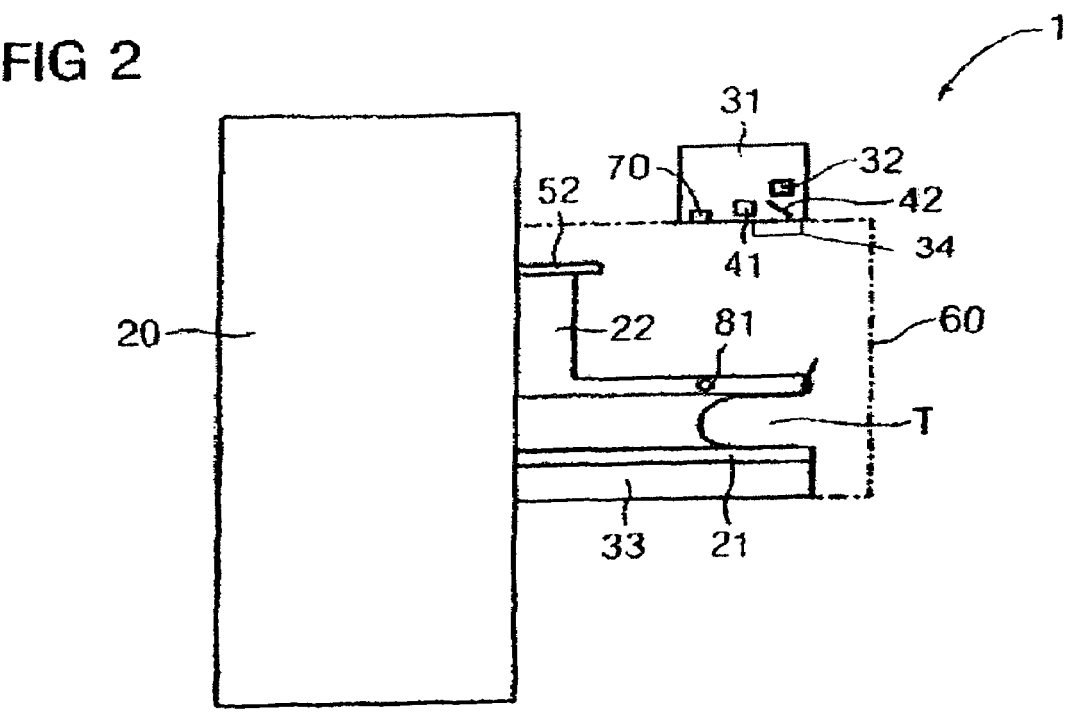
FIG. 2 is a side view of one embodiment of an X-ray device with a second light source mounted on the support arm.

In one embodiment, as shown in FIG. 2, the mammography device 10 includes a support arm 20, on which an object table 21 and a compression unit 22 are mounted. An emitter head 31 is disposed above the object table 21. The emitter head 31 has an X-ray source 32. The X-radiation generated by the X-ray source 32 is emitted in the direction of the object table 21 through the opening in a diaphragm 34 and shines through the examination part T of the examination object that is positioned on the object table 21. The X-radiation is detected by an X-ray detector 33 disposed below the object table 21.

In one embodiment, as shown in FIG. 2, a first light source 41 is installed in the emitter head 31. The first light source 41 may be a point-shaped light source. The first light source 41, illuminates the surface region through which the X-radiation shines when the X-radiation is activated. The first light source 41 may be activated by a control key. In one embodiment, a mirror 42 is pivoted into the beam path of the first light source 41 and deflects the light from the first light source 41 in the direction of the object table 21 when the first light source 41 is activated. The light from the first light source 41 passes through the opening in the emitter head 31 and also passes at least partway through the opening in the diaphragm 34. The first light source 41 projects a light marking of the beam field of the X-radiation on the object table 21, or on the examination part T of the examination object.

In one embodiment, as shown in FIG. 2, a second light source 52 is mounted on the support arm 20, such as on the compression unit 22. The second light source 52 may be activated (switched on) via a motion sensor 70, for example, as soon as motion in the work region 60 is detected. For example, the second light source 52 is activated if work must be done on the examination object or on the object table 21 before or during the X-ray examination. In one embodiment, the sensitivity of the motion detector 70 to motion is adapted (set) such that at relatively small motions of the examination object, no tripping of the work region 60 lighting or of the second light source 52 takes place.

In one embodiment, the support arm 20 includes additional components, for example, a tube holder, not shown, which for instance holds the emitter head 31, the object table 33, and the compression unit 22, and on which the work lighting may be disposed.

In one embodiment, the second light source 52 remains on as long as the motion sensor 70 senses (records) motion in the work region 60. In one alternate embodiment, the second light source 52 is integrated into the object table 21. In this embodiment, the object table 21 is transparent, so that the examination part T of the examination object can be lighted from below. In this embodiment, only a limited intensity may be achieved because there may be a glare on the examination object or for the medical worker, which would make the work more difficult.

If the second light source 52 is suitably mounted in the upper region of the compression unit 22, glare affecting both the medical worker and the examination object can be avoided. For example, the second light source 52 may be embodied as a number of light-emitting diodes, which emit light in various directions and thus assure adequate lighting of the work region 60.

In one embodiment, a plurality of second light sources may be mounted on the X-ray device 1. For example, in one embodiment, a second light source 51 may be provided on the emitter head 31, as shown in FIG. 1; a further second light source may be mounted on the compression unit 22, as shown in FIG. 2,; the second light source 53 may be also mounted on the object table 21 (FIG. 3), or the second light source 54 may be mounted below a transparent surface of the object table 21 (FIG. 4). The light sources are not limited to this arrangement. The second light source may be disposed at any suitable location. For example depending on the visual task or on the work to be done in the work region 60 of the X-ray device 1, various positioned light sources and also various kinds of light sources can be used. The first and second light sources may be embodied as any suitable light source, for example, incandescent lamps or low-voltage halogen lamps.

In one alternative embodiment, a user-control device 81 may be provided which switches the second light source 52 on and off, for example, in contactless fashion. The user-control device 81 can be equipped with a sensor, not shown, which uses, for example, infrared radiation, light intensity, or light signal transmit times in order to enable contactless operation of the light source 52.

In one embodiment, as shown in FIG. 2, one contactless user-control device 81 is mounted on the compression unit 22. This kind of user control element 81 is beneficial in work regions 60 that require sterile conditions. A requirement for sterile conditions exists when a medical intervention is completed, for example, a biopsy.

In one embodiment, when the first light source 41 is activated and marks the area, which is to be irradiated by the X-ray source 32, the second light source 51 and/or 52 is not switched on. As a result, the marking with adequate luminous intensity of the area to be irradiated can be assured.

The invention claimed is:

1. A device for imaging an examination part of an object to be examined, comprising:
    an x-ray device, further comprising:
    a support arm that supports an emitter head and an X-ray detector, the emitter head including an X-ray source;
    a first light source that is operative to illuminate a surface, which is to be irradiated by the X-ray source, of the examination part; and
    a second light source that is operative to illuminate a work region in which the examination part is positionable for the imaging,
    wherein the first light source and the second light source are not X-ray sources, and the first and second light sources are attached to the X-ray device.

2. The device as defined by claim 1, wherein the second light source has a greater luminous intensity than the first light source.

3. The device as defined by claim 1, wherein the second light source has a light cone with a larger opening angle than the first light source.

4. The device as defined by claim 1, wherein the second light source is connected to the support arm.

5. The device as defined by claim 1, wherein the second light source is connected to the emitter head.

6. The device as defined by claim 1, wherein the second light source comprises a light-emitting diode.

7. The device as defined by claim 1, wherein the second light source is displaceable or rotatable relative to the support arm.

8. The device as defined by claim 1, wherein the second light source is operatively coupled to a user-control device, which is disposed near the illuminatable work region.

9. The device as defined by claim 1, wherein the second light source is operative in contactless fashion.

10. The device as defined by claim 1, wherein the second light source is displaceable and rotatable relative to the support arm.

11. The device as defined by claim 1, wherein the X-ray device comprises a mammography device.

12. The device as defined by claim 1, wherein a motion sensor operatively couples to the second light source.

13. The device as defined by claim 1, wherein the second light source is disposed below an examination part of an examination object.

14. The device as defined by claim 13, wherein the second light source is disposed on an object table coupled to the support arm.

15. The device as defined by claim 1, comprising an object table and compression unit coupled to the support arm.

16. The device as defined by claim 15, wherein the second light source comprises a plurality of light sources, and wherein one of the plurality of second light sources is disposed on the emitter head, another of the plurality of second light sources is disposed on the compression unit, and another of the plurality of second light sources is disposed on the object table.

17. The device as defined by claim 2, wherein the second light source has a light cone with a larger opening angle than the first light source.

18. The device as defined by claim 17, wherein the second light source comprises a light-emitting diode.

19. The device as defined by claim 4, wherein the second light source is displaceable or rotatable relative to the support arm.

20. The device as defined by claim 1, wherein a light cone angle of the first light source is approximately equal to a radiation cone angle of the X-ray source.

21. The device as defined by claim 1, wherein the second light source is fixedly attached to the X-ray device.

* * * * *